United States Patent [19]

Egger et al.

[11] Patent Number: 4,675,728
[45] Date of Patent: Jun. 23, 1987

[54] APPARATUS FOR PERFORMING INTERNAL INSPECTION OF PIPING

[75] Inventors: Eugene R. Egger, Baldwinsville, N.Y.; Harold Sherman, Toledo, Ohio

[73] Assignee: C.T.S. Consulting Personnel Svcs., Inc., Liverpool, N.Y.

[21] Appl. No.: 707,493

[22] Filed: Mar. 1, 1985

[51] Int. Cl.⁴ ............................................. H04N 7/18
[52] U.S. Cl. ................................ 358/100; 250/459.1; 250/461.1; 358/106; 358/110
[58] Field of Search ................. 358/100, 110, 106, 98, 358/99; 250/461.1, 459.1; 356/237

[56] References Cited

U.S. PATENT DOCUMENTS

| | | | |
|---|---|---|---|
| 3,499,107 | 3/1970 | Sheldon | 358/98 |
| 4,011,174 | 3/1977 | Molina | 250/459.1 |
| 4,194,218 | 3/1980 | Hasegawa | 358/100 |
| 4,272,781 | 6/1981 | Taguchi | 358/100 |
| 4,460,920 | 7/1984 | Weber | 358/100 |
| 4,536,654 | 8/1985 | Vaerman | 250/461.1 |

*Primary Examiner*—Howard W. Britton
*Attorney, Agent, or Firm*—Charles S. McGuire

[57] ABSTRACT

A carriage is designed for transport into and out of a pipe, carrying appropriate lighting and a television camera with a lens cover movable from a remote location between covering and uncovering positions. A movable portion carrying two sets of three nozzles, one of each set being equipped to emit a spray of water, liquid penetrant and air, is mounted on the carriage. After an initial visual inspection on a remote TV monitor to verify location and check for the presence of relatively large cracks or flaws, the lens is covered, the inside pipe surface is sprayed first with water for cleaning, then with penetrant which enters any cracks which may be present, and again with water to wash away any penetrant other than that which has entered cracks in the area being inspected. The surface is then dried by the air nozzle, the lens cover removed and a "black light" source turned on, thus rendering visible on the TV monitor any liquid penetrant which is entrapped in small cracks or faults in the pipe. A radioactive substance may also be carried on the device and used for supplementary inspection by wrapping a photographic film on the exterior of the pipe.

13 Claims, 7 Drawing Figures

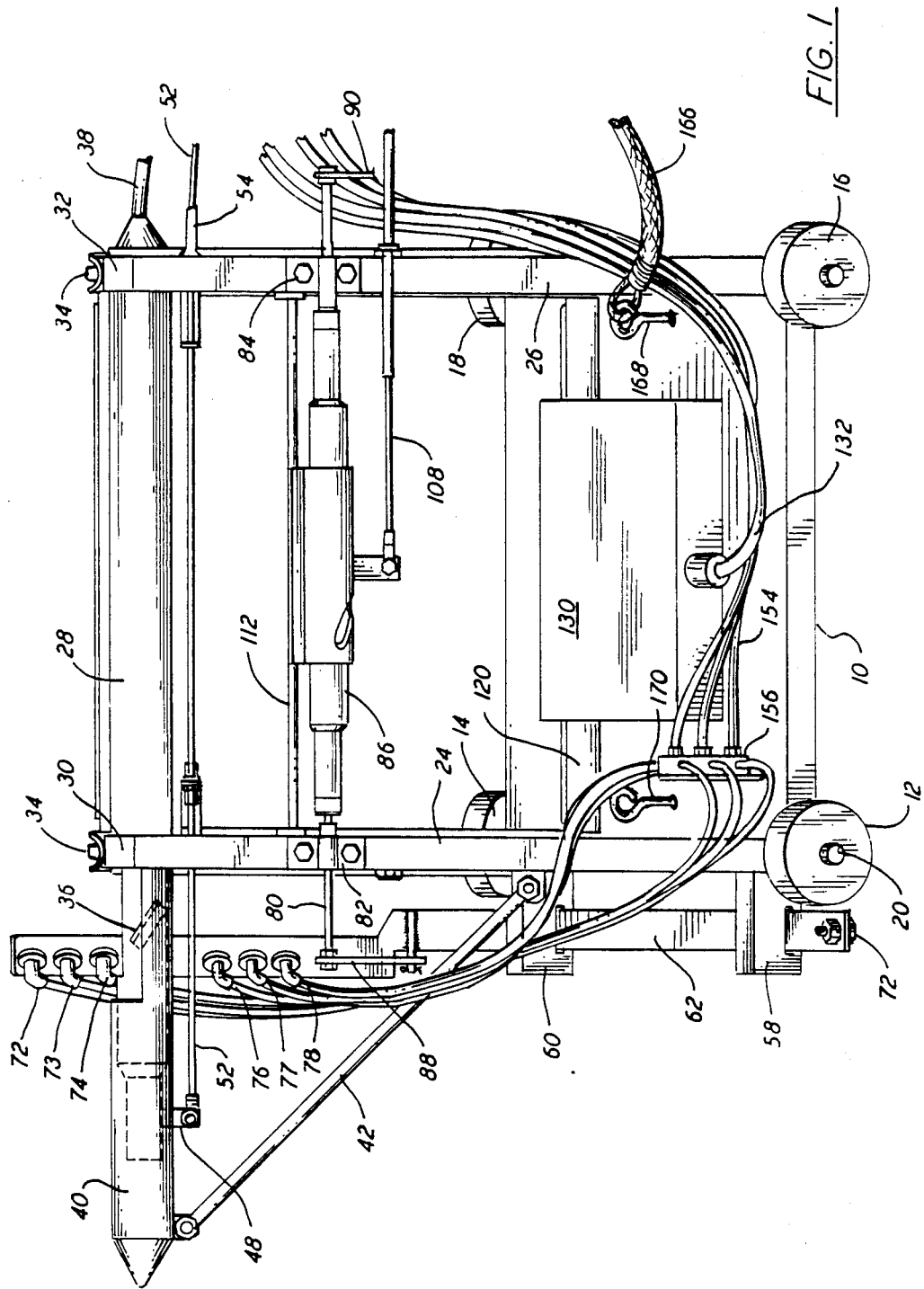

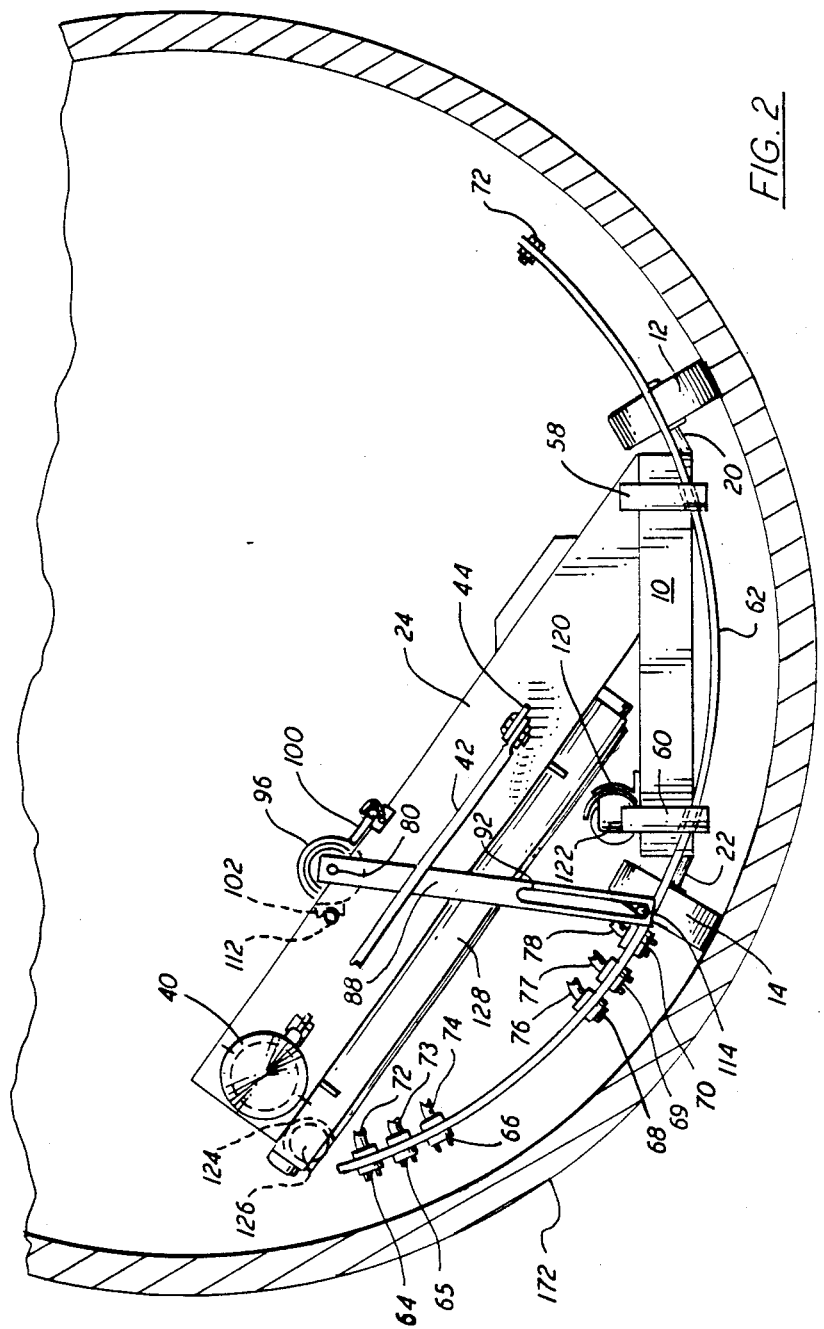

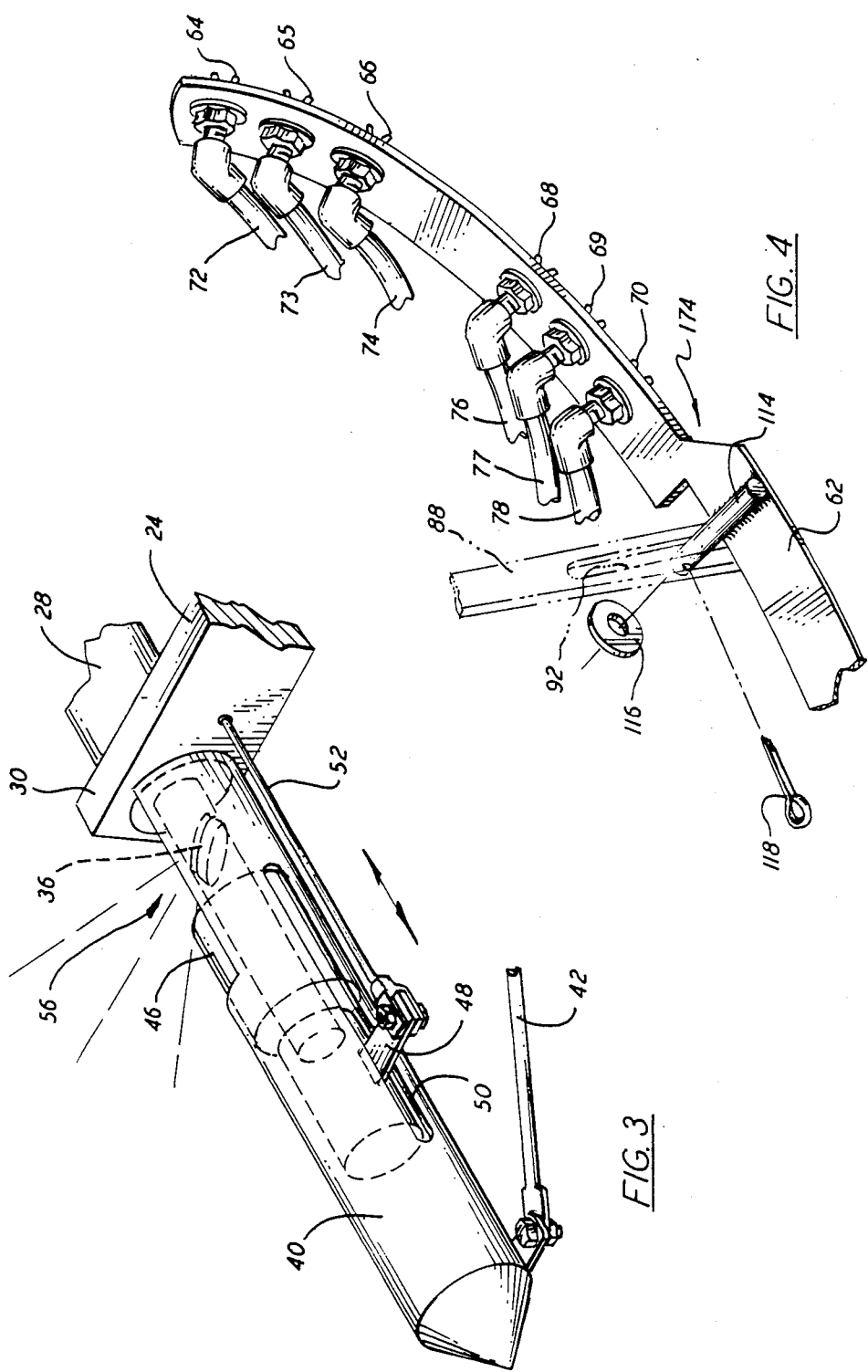

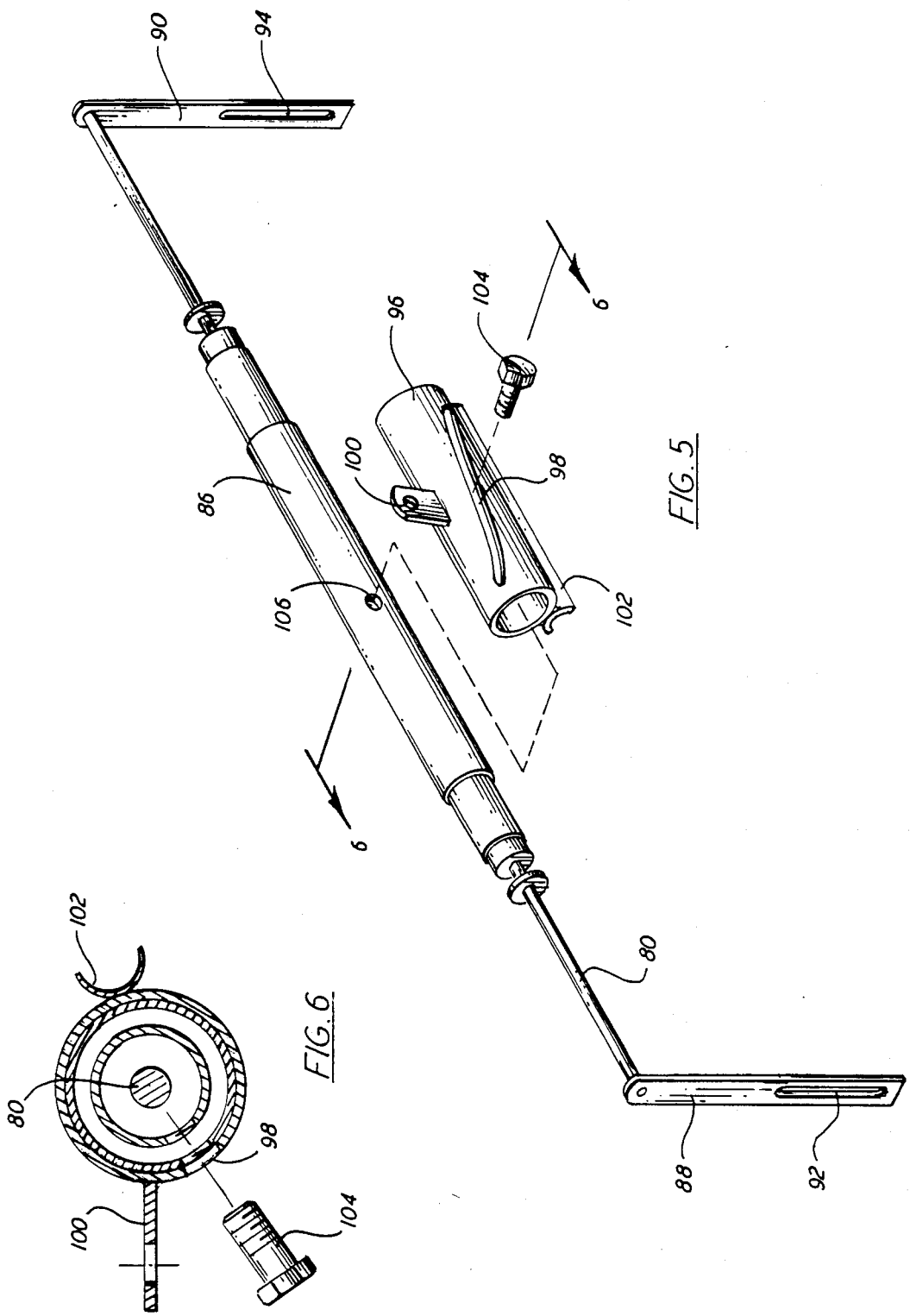

4,675,728

APPARATUS FOR PERFORMING INTERNAL INSPECTION OF PIPING

BACKGROUND OF THE INVENTION

The present invention relates to inspection of piping for cracks or flaws, and more particularly to apparatus and methods facilitating visual inspection of the piping used in nuclear power generating operations, and the like.

Piping such as that used in nuclear power generating facilities must be inspected prior to use and periodically thereafter to determine whether any cracks or flaws are present, e.g., at welded locations, which could indicate an actual or potential hazardous condition. Conventional means of performing such inspections have included placing a radioactive material on one side and a photographic film on the other side, both exteriorly of the pipe, and ultrasonic means. In the former, it is necessary that the radiation pass through two layers of the piping material at the location being inspected before reaching the film, and the process must be repeated a number of times in order to obtain a complete scan of 360° at a given pipe location. While ultrasonic means are effective in detecting irregularities in the pipe surface, such irregulatiries may be due to normal conditions within the pipe rather than cracks or other faults in the weld or pipe. A totally acceptable means of direct visual inspection has not been practical. In any case, inspection operations of this type have traditionally been very time-consuming and expensive in order to obtain a reliable determination of the presence of potentially dangerous cracks or other faults in the line.

It is a principal object of the present invention to provide a safe, reliable and relatively fast and inexpensive means of inspecting the interior of piping used in nuclear power generating operations for the presence of cracks and faults.

Another object is to provide apparatus for permitting direct visual inspection of the interior of piping to identify any cracks, including minute cracks not normally visible to the naked eye.

A further object is to provide apparatus including a television camera suitable for transport into and out of piping of a nuclear power plant to permit visual inspection of the interior of the piping from a remote location.

Still another object is to provide a reliable apparatus for transmitting an image of the interior of a pipe surface to a remote television monitor which effectively displays for immediate visual identification substantially all minute cracks or flaws which are present on the entire internal periphery of the pipe at a given location along its length.

Other objects will in part be obvious and will in part appear hereinafter.

SUMMARY OF THE INVENTION

In accordance with the foregoing objects, the invention is performed with apparatus including a rigid frame mounted upon two pairs of wheels adapted for rolling contact with the interior of the piping to be inspected, whereby the apparatus may be transported into and out of the piping regardless of the orientation thereof (i.e., vertical, horizontal or at any other angle). The disclosed embodiment includes a pair of parallel frame members extending at an acute angle to the frame portions between each set of wheels. A conventional television camera of the type including a built-in light source and a rotatable mirror for viewing a field at 90° to the camera axis is mounted upon the parallel frame members, and connected to a remote monitor. A cap is selectively movable from a remote location, by means of a connecting cable, between covering and uncovering positions with respect to the camera lens and mirror.

An arcuate bar having a radius of curvature equal to that of the pipe to be inspected is mounted for movement through slots in a pair of members extending from the lower portion of the frame at the end toward which the camera faces. Means are provided for moving the bar from a location outside the pipe along a limited arc concentric with the pipe surface, i.e., along the arcuate axis of the bar. Two sets of three nozzles each are carried upon the arcuate bar to direct a spray upon the adjacent portion of the interior pipe surface. One nozzle of each set is connected to a pressurized source of water, or other cleaning solution, one to a source of liquid penetrant and one to a source of compressed air. Mechanical linkage means are provided for transmitting linear movement of a control cable to arcuate movement of the bar in order to move the nozzles relative to the pipe surface. A plurality of "black light" sources are mounted upon the frame for selective actuation from a remote location.

In practising the invention, the apparatus is transported into the piping to a position adjacent the area to be inspected. The position of the apparatus relative to the pipe may be visually verified by moving the lens/mirror cap to the uncovering position and turning on the camera. The position is observed on the remote monitor while, at the same time, visually inspecting the area for any large cracks or faults. The camera is then turned off and the cap replaced. The area to be inspected is cleaned by spraying with water and then sprayed with the liquid penetrant which enters any small cracks, holes or other flaws in the adjacent surface of the pipe. The area is again sprayed with water to remove all penetrant except that which has entered the cracks, etc. and thereafter dried by the air nozzle. The lens/mirror cap is then removed, the camera and black lights turned on, and the visual inspection conducted by scanning the camera over the area and observing on the monitor the presence of any penetrant which fluoresces under the black light. The process may be repeated, as desired, after movement of the nozzle mounting bar to a new position for inspection of additional areas about the periphery of the pipe.

The construction of the apparatus is such that it presents a low profile, being adapted for transport through a portion of the pipe equal to about ⅓ of its diameter, while permitting inspection of approximately 110° about the periphery of the pipe without removing the apparatus from the pipe for repositioning. The positions of the camera and nozzle bar movement linkage may be reversed on the parallel frame members, and a nozzle bar with the positions of the nozzles reversed mounted at the opposite end of the frame to permit inspection of the opposite side of the pipe.

BRIEF DESCRIPTION OF THE DRAWINGS

FIG. 1 is a side perspective view of an embodiment of the apparatus of the invention;

FIG. 2 is a front elevational view of the apparatus of FIG. 1, shown inside a fragment of piping;

FIG. 3 is a fragmentary, perspective view of the camera lens/mirror cover operating mechanism;

FIG. 4 is a fragmentary, perspective view of the nozzle bar mounting means;

FIG. 5 is an exploded, perspective view of the motion transmission mechanism for the nozzle bar;

FIG. 6 is an end elevational view in section on the line 6—6 of FIG. 5; and

DETAILED DESCRIPTION

Figure 7:
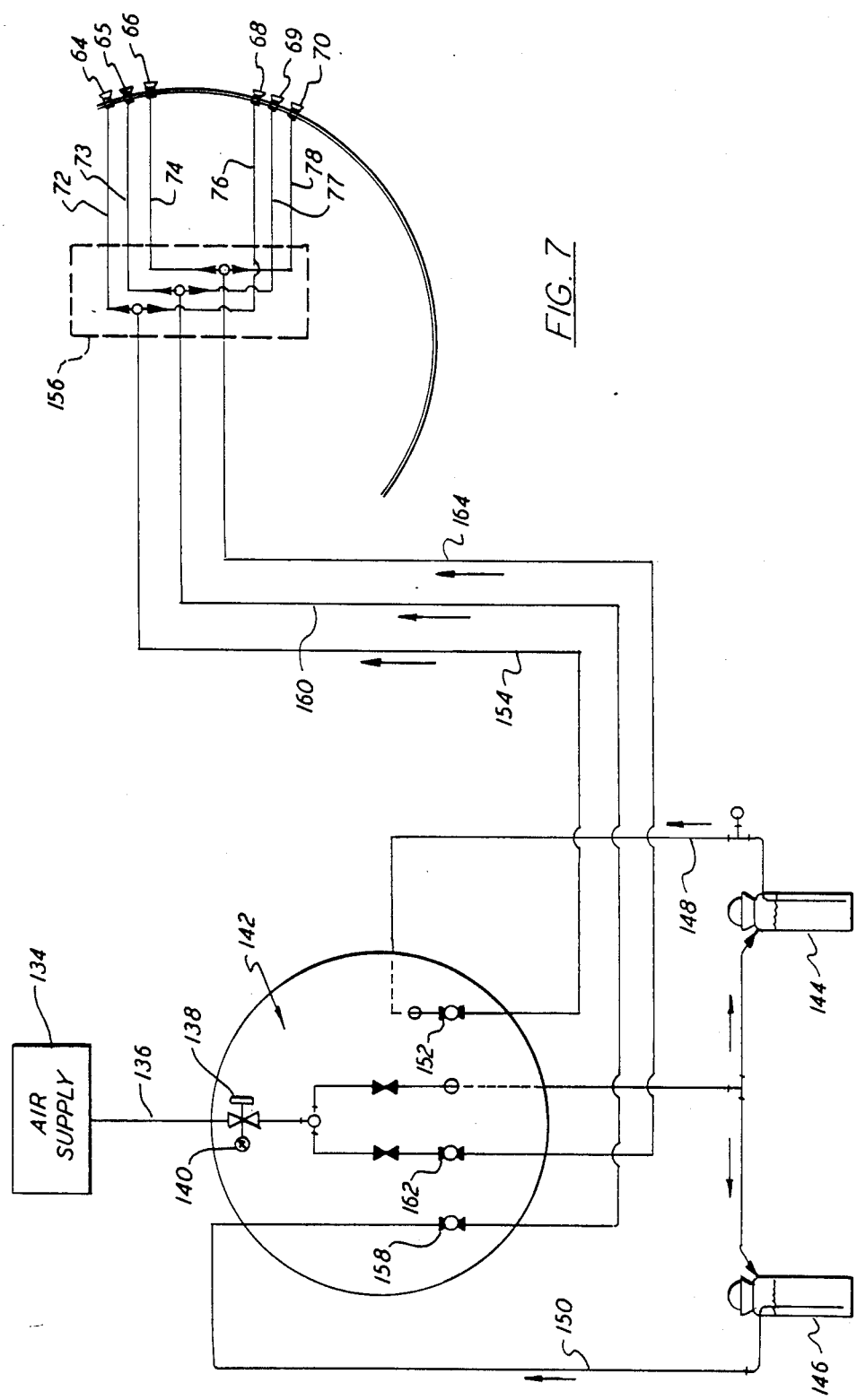
FIG. 7 is a schematic diagram showing the manner of operation of the spray nozzle system.

Referring now to the drawings, the invention will be described with reference to an embodiment of apparatus through which the internal pipe inspection is performed. In the intended applications and environment of nuclear power plant piping inspection, it is preferred that the entire assembly be constructed of stainless steel. Lower frame member 10 is mounted upon a first pair 12 and 14, and a second pair 16 and 18 of wheels. First wheels 12 and 14 are rotatable on axles 20 and 22, respectively, and second wheels 16 and 18 on similar axles, welded to frame member 10 to extend along axes perpendicular to a line radial to a pipe of the size to be inspected with the use of the apparatus.

Parallel frame mexbers 24 and 26 are welded at one end to lower frame member 10 and extend upwardly at an acute angle thereto, as best seen in FIG. 2. Conventional television camera 28 is mounted at the upper ends of members 24 and 26 by means of upper end portions 30 and 32 which are secured by cap screws 34, providing close fitting openings for the cylindrical camera housing. Camera 28 is of a commercially available type having mirror 36 arranged in front of the camera lens, at 45° to the axis thereof, and a built-in motor for rotating the lens, whereby the field of view of the camera is scanned about a field at 90° to the camera axis. The camera also includes an integral light source (not shown). Electrical cable 38 extends from camera 28 to a remote control unit for control of power (on/off), focus, scanning motor, light source, etc.

Housing 40 is supported at one end by frame member 24, extending forwardly therefrom to a second end, supported by brace 42 extending from the housing second end to bracket 44 on frame member 24. Housing 40 is hollow for reciprocal sliding movement therein of lens/mirror cap 46 between covering and uncovering positions with respect to the camera lens and mirror 36. As best seen in FIG. 3, arm 48 extends from cap 46 through slot 50 in housing 40 and is attached to control cable 52. The latter extends through openings in frame members 24 and 26, and through flexible sleeve 54 (FIG. 1) to a terminal end at a remote location for movement by an operator to effect movement of the cap between its covering and uncovering positions as indicated by the arrows in FIG. 3. A portion of housing 40 is cut away in the area adjacent mirror 36, denoted in FIG. 3 by reference numeral 46, to permit viewing by the camera during scanning movement of the mirror through the necessary arc of rotation.

Support members 58 and 60 are bolted to one end of lower frame mexber 10, and each includes a slot for passage of arcuate bar 62. A first set of three nozzles 64, 65 and 66 are mounted upon bar 62 adjacent one end thereof, and a second set of nozzles 68, 69 and 70 are mounted upon the bar at a position spaced an appropriate distance from the first set. Stop bolt 72 is secured at the other end of bar 62 to limit movement thereof through the slot in support member 58. One nozzle of each set is connected to a source of water or other cleaning solution, one to a source of liquid penetrant and one to a source of compressed air. For example, nozzles 64, 65 and 66 are connected to the water, penetrant and air sources by hoses 72, 73 and 74, respectively, and nozzles 68, 69 and 70 are connected to the same respective sources by hoses 76, 77 and 78.

Bar 62, and thus the two sets of nozzles, is reciprocally movable along its own arcuate axis by means which will now be described. Shaft 80 is supported for rotation in brackets 82 and 84, attached to frame members 24 and 26, respectively, passing through and being fixedly attached to hollow tubing 86. Linkage bars 88 and 90 are fixedly attached to opposite ends of shaft 80, extending downwardly therefrom, and include elongated slots 92 and 94, respectively. Hollow pipe 96 encircles tubing 86 for sliding movement thereon, and includes curved cam slot 98. Fixed arm 100 extends from one side of pipe 96 and arcuate follower member 102 is welded to the other side. Bolt 104 passes loosely through cam slot 98 and is secured in threaded opening 106 in tubing 86. Cable 108 is attached at one end to arm 100 and extends through flexible sleeve 110, attached to frame member 26, to a terminal end at a remote location for movement by an operator. Follower 102 rests upon fixed guide shaft 112, extending between frame members 24 and 26, for sliding movement thereon. Thus, linear movement of cable 108 is transmitted to pipe 96 and translated to rotational movement of tubing 86 and shaft 80 by movement of bolt 104 about the axis of shaft 80 as constrained by the shape of cam slot 98. Pin 114 is welded to bar 62 and extends forwardly therefrom, through slot 92 in link 88, secured by washer 116 and cotter pin 118, as seen in FIG. 4. Rotation of shaft 80 is thus transmitted through link 88 to bar 62.

Also mounted upon the framework of the apparatus are an appropriate number of light sources emitting wavelengths in the area commonly known as "black light." In the illustrated embodiment, for example, four elongated, flourescent tubes are mounted in conjunction with stainless steel reflectors. One such reflector and tube combination, indicated by reference numerals 120 and 122, respectively, extends along one side of lower frame portion 10. A second reflector 124 and tube 126 extend between frame members 24 and 26 adjacent camera 28. Third and fourth reflectors and bulbs extend along the lower sides of frame members 24 and 26, the reflector attached to frame member 24 being shown in FIG. 2 and denoted by reference numeral 128. Junction box 130, containing the necessary starter, transformer and power supply circuitry for the light sources, is mounted upon frame portion 10 and connected to a remote power source by cable 132.

Referring now to FIG. 7, compressed air source 134 is connected by line 136 to regulator 138 and pressure gauge 140 at a control panel, diagrammatically indicated at 142. The air supply communicates, through appropriate valves and fittings, with a pair of metal tanks 144 and 146, containing water and a liquid penetrant such as the fluorescent penetrant manufactured and sold by the Turco Division of the Purex Company, respectively, thereby pressurizing discharge lines 148 and 150 of the two tanks. Water line 148 is connected to manually controlled valve 152 at control panel 142, and thence through line 154 to manifold 156, shown also in FIG. 1, through which it is connected to both lines 72 and 76, leading to nozzles 64 and 68, respectively. Penetrant discharge line 150 is connected through control valve 158 to manifold 156 by line 160, and thence to lines 73 and 77 and nozzles 65 and 69. Air supply 134 is connected to control valve 162 and to manifold 156 through line 164, and thence to lines 74 and 78 and nozzles 66 and 70.

In performing the internal piping inspection according to the present invention, the apparatus is inserted into the section of piping until it reaches a position adjacent the particular area to be inspected, often a weld in the pipe line. All of the various lines, cables, etc. by which the apparatus is connected to the control location outside the pipe are gathered together to form a composite "umbilical cord" which may be used for lowering the apparatus into a vertical or inclined pipe, or for pushing it into a horizontal pipe. Dimensional markings on the umbilical cord may be used to approximate the position of the apparatus in the pipe. Also, safety cord 166 is preferably attached to one of two lifting lugs 168 and 170 affixed to lower frame portion 10.

The low profile design of the apparatus allows passage through the gate valves typically employed in the piping of nuclear generating facilities which may require, for example, a maximum raidal height of the apparatus within the pipe of 8" for a pipe having a 24" diameter. The apparatus is shown in FIG. 2 positioned in a section of pipe 172 adjacent an area thereof to be inspected for cracks, or other flaws. The apparatus is inserted into pipe 172 with lens/mirror cap 46 in the covering position to avoid damage to these portions of the camera. When the apparatus has been transported into the pipe to a position adjacent the area to be inspected, cap 46 is moved to the uncovering position by manipulation of cable 52 at the control location and power to camera 28 is turned on. The display on the TV monitor will then indicate the exact position of the apparatus and any necessary adjustments may be made to bring the apparatus to the position required in order for the camera to view the area to be inspected. Also, the area may be visually inspected at this time for any relatively large cracks or flaws.

Cap 46 is then returned to the covering position and valve 152 is opened to provide water spray through nozzles 64 and 68 in order to wash away any foreign matter from the area to be inspected. Valve 152 is then closed and valve 158 opened to spray liquid penetrant over the inspection area within pipe 172. The nature of the penetrant is such that it will enter, and become entrapped in, any tiny cracks or flaws in the area covered by the spray. Valve 158 is closed and valve 152 is opened again so that the water spray will carry away all penetrant on the inner surface of the pipe other than that which has entered the small cracks. Valve 152 is closed and valve 162 is opened so that the area is essentially dried by the air spray, and valve 162 is then closed, the area now being prepared for inspection.

Cap 46 is moved to the uncovering position and power to both the camera and the "black light" sources is turned on. As the camera motor rotates mirror 36 the area under inspection is scanned and the image transmitted by camera 28 is displayed on the TV monitor at the control station. Any penetrant which has been entrapped in cracks or flaws in the inspection area of pipe 172 will be readily visible under the black light which illuminates the inspection area. Nozzle support bar 62 may then be moved in the manner previously described and the process repeated. It will be noted that bar 62 is offset in the area indicated in FIG. 4 by reference numeral 174, thereby providing an area of unobstructed view for scanning by mirror 36. Also, the nozzles are inclined with respect to bar 62 to direct their sprays upon the viewing area.

With the apparatus positioned within a pipe as shown in FIG. 2, an arcuate portion, extending approximately 120° around the internal periphery of the pipe and having a width of about 3", may be inspected in two steps, i.e., with bar 62 positioned first at one end and then re-positioned at the other end of its movement. A like segment on the opposite side of the pipe may be inspected by reversing the position of certain parts of the apparatus, as described in the following paragraph.

Upper portions 30 and 32 of frame members 24 and 26 are removed, cable 52 disconnected and withdrawn from the frame members, and brace 42 disconnected from frame member 24. Camera 28 and housing 40 are reversed end-for-end and replaced on the frame members, cable 52 is inserted in the opposite direction through the frame members and re-attached to arm 48, and brace 42 is attached to frame member 26. Support members 58 and 60 are unbolted from the end of frame portion 10 and bolted to the opposite ehd and a nozzle support bar similar to, but offset in the opposite direction from, bar 62 is positioned in the support member slots. Pin 114 on the nozzle support bar is positioned through slot 94 in link 90 at the opposite end of shaft 80 and cable 108 is connected to arm 100 from the opposite direction. With the elements so positioned, the apparatus is inserted into pipe 172 reversed end-for-end from that shown in FIG. 2, i.e., so that the re-positioned camera and nozzle support bar are at the other end. The inspection procedure previously described may then be repeated to effect visual inspection of portion 176. The lower portion of pipe 172, designated by reference numeral 178, between portions 174 and 176, may be inspected by positioning the apparatus in a circumferentially offset position from that shown in FIG. 2.

From the foregoing, it may be seen that the objects of the invention are efficiently achieved, providing a practical, fast and economical procedure for direct visual inspection of the interior of piping, having particular utility in the field of nuclear power generating facilities. The disclosed apparatus provides a hardware package of unique design through which the invention is implemented. Since the apparatus provides access to the interior of the piping, the inspection may be expanded to include fault detection by photographic means simply by placing a radioactive material on the apparatus and wrapping a photographic negative on the exterior of the pipe adjacent the interior position of the apparatus.

What is claimed is:

1. Apparatus for use in visually inspecting the interior of piping of predetermined diameter used in nuclear power generating facilities for cracks and other faults, said apparatus comprising, in combination:
   (a) rigid frame means;
   (b) means for transporting said frame means into and out of said piping;
   (c) a television camera mounted upon said frame means and adapted to scan an arcuate field of view about at least a portion of the internal surface of said piping adjacent which said frame means is positioned and to electronically transmit an image of said surface for display on a CRT monitor exteriorly of said piping;
   (d) a plurality of spray nozzles mounted upon said frame means and adapted to direct respective sprays over common portions of said camera field of view;

(e) a supply of liquid penetrant capable of entering any cracks or faults to be detected in said internal surface connected to at least a first of said spray nozzles;

(f) a supply of water or other cleaning solution connected to at least a second of said spray nozzles;

(g) means for selectively acutating said first and second spray nozzles to sequentially direct sprays of said penetrant and said water over said common portions; and (h) black light means mounted upon said frame means and selectively actuable to illuminate said field of view of said camera and to render visible, in contrast to the surrounding area, said liquid penetrant which enters said cracks or faults, whereby said internal surface may be visually inspected by identifying said liquid penetrant on said CRT monitor.

2. The invention according to claim 1 and further including a supply of pressurized air connected to at least a third of said spray nozzles, and means for actuating said third spray nozzle to direct an air spray over said common portions.

3. The invention according to claim 2 wherein one of each of said first, second and third spray nozzles are provided in two respective groups, arranged to direct sprays of penetrant, water and air over two adjacent common areas of said internal surface of said piping.

4. The invention according to claim 1 and further including mounting means for said spray nozzles and means for selectively moving said mounting means relative to said frame means, whereby said spray nozzles may be moved to direct their respective sprays over different common areas.

5. The invention according to claim 4 wherein said mounting means comprise an arcuate bar having a radius of curvature equal to that of the piping to be inspected and arranged concentrically therewith when said frame means is positioned inside said piping in position for visually inspecting said internal surface thereof.

6. The invention according to claim 5 wherein said means for moving said mounting means comprises a mechanical linkage including a rod having an end portion positioned exteriorly of said piping for manual manipulation to effect movement of said mounting means, and thereby said nozzles, relative to said frame means.

7. The invention according to claim 1 and further including a lens cap for said television camera and means for selectively moving said lens cap between covering and uncovering positions with respect to the lens of said camera.

8. The invention according to claim 7 wherein said means for moving said lens cap comprises a mechanical linkage including a rod having an end portion positioned exteriorly of said piping for manual manipulation to effect movement of said lens cap between said covering and uncovering positions.

9. The invention according to claim 1 wherein said means for transporting said frame means comprise a plurality of wheels upon which said frame means is mounted and a line attached to said frame means and extending outside said piping, said line having sufficient rigidity to permit transport of said frame means into and out of said piping by manually pushing or pulling on said line from a position exteriorly of said piping.

10. The invention according to claim 9 wherein said supplies of liquid penetrant and water are connected to said spray nozzles by respective hoses and said hoses are gathered together to provide said line.

11. The invention according to claim 10 wherein the overall vertical height of said apparatus when resting on said wheels is not greater than about one-third of said predetermined diameter.

12. The invention according to claim 11 wherein said frame means comprises a lower frame member mounted upon said wheels, and at least one upper frame member rigidly attached to said lower frame member and extending upwardly therefrom at an acute angle, said camera being mounted upon said upper frame member.

13. The invention according to claim 12 wherein said camera is selectively mountable upon said upper frame member in either of two positions, with the camera lens directed toward opposite ends of said frame means, and said spray nozzle, are selectively mountable upon the end of said frame means toward which said camera lens is directed.

* * * * *